United States Patent [19]
Termin et al.

[11] Patent Number: 6,086,603
[45] Date of Patent: Jul. 11, 2000

[54] LUMINAL PORT DEVICE HAVING INTERNAL AND EXTERNAL SEALING MECHANISMS

[75] Inventors: Charles S. Termin, Miami; Kevin W. Smith, Coral Gables; Charles R. Slater, Fort Lauderdale; Saul Gottlieb, Miramar, all of Fla.

[73] Assignee: Syntheon, LLC, Miami, Fla.

[21] Appl. No.: 09/211,175

[22] Filed: Dec. 14, 1998

[51] Int. Cl.[7] .................................................. A61M 37/00
[52] U.S. Cl. ........................... 606/191; 606/185; 604/164
[58] Field of Search ................................ 606/1, 184, 185, 606/191, 192, 193; 604/164, 167, 174, 264

[56] References Cited

U.S. PATENT DOCUMENTS

| | | |
|---|---|---|
| 4,649,913 | 3/1987 | Watson . |
| 4,856,510 | 8/1989 | Kowalewski . |
| 5,002,557 | 3/1991 | Hasson . |
| 5,241,956 | 9/1993 | Brain . |
| 5,342,385 | 8/1994 | Norelli et al. . |
| 5,391,156 | 2/1995 | Hildwein et al. . |
| 5,513,627 | 5/1996 | Flam . |
| 5,520,698 | 5/1996 | Koh . |
| 5,624,399 | 4/1997 | Ackerman . |
| 5,632,761 | 5/1997 | Smith et al. . |
| 5,634,911 | 6/1997 | Hermann et al. . |
| 5,634,937 | 6/1997 | Mollenauer et al. . |
| 5,637,097 | 6/1997 | Yoon . |
| 5,643,285 | 7/1997 | Rowden et al. . |
| 5,653,726 | 8/1997 | Kieturakis . |
| 5,674,239 | 10/1997 | Zadini et al. . |
| 5,704,372 | 1/1998 | Moll et al. . |
| 5,722,983 | 3/1998 | Van Der Weegen . |
| 5,730,725 | 3/1998 | Yoon . |

FOREIGN PATENT DOCUMENTS

| | | |
|---|---|---|
| 599-811 | 3/1978 | U.S.S.R. . |

*Primary Examiner*—Michael Buiz
*Assistant Examiner*—William W. Lewis
*Attorney, Agent, or Firm*—David P. Gordon; David S. Jacobson; Thomas A. Gallagher

[57] ABSTRACT

A luminal port assembly insertable into an anatomical passageway includes a housing having a seal which creates a fluid-tight seal between the housing and the tissue of the anatomical passageway. At least one port is provided in the housing. Each port is preferably angularly movable relative to the housing and includes a substantially fluid-tight valved passageway and an insufflation conduit. A mechanism for retaining the luminal port assembly within the anatomical passageway is also provided.

41 Claims, 10 Drawing Sheets

LUMINAL PORT DEVICE HAVING INTERNAL AND EXTERNAL SEALING MECHANISMS

BACKGROUND OF THE INVENTION

1. Field of the Invention

This invention relates broadly to surgical devices. More particularly, this invention relates to a surgical device which provides a valved port in an anatomical passageway.

2. State of the Art

A vaginal hysterectomy is a hysterectomy performed through the anatomical passageway of the vagina without necessitating an abdominal incision. During the procedure, blood vessels nourishing the uterus and the ligaments supporting the uterus are tied off at the various points with sutures. The uterus is then surgically removed via the vagina. Methods for uterine removal are discussed in U.S. Pat. No. 5,520,698 to Koh which provides a complex apparatus for the disclosed methods. The Koh device generally includes an occluder provided with an opening, and a vaginal extender and uterine manipulator extending through the opening. The extender and manipulator are provided in the vagina where they provide anatomical landmarks to aid in colpotomy incision and uterine manipulation. Surgical instruments are then inserted laparoscopically through an abdominal incision into an insufflated abdominal cavity and using the extender and manipulator as guides and colpotomy incision backstops, and excise the uterus. However, the device includes several drawbacks which limits its use. First, if the extender and manipulator are removed from the occluder, the opening becomes a fluid passage. As such, the device cannot be used to retain an insufflation gas in the abdominal cavity after a hysterectomy unless the extender and manipulator remain within the opening, which obstructs the passage of other instruments therethrough. Second, when using the occluder in an insufflated environment, an obtrusive external handle is required to hold the occluder in place and counter pressure which would otherwise force the occluder out of the vaginal passageway.

After the removal of the uterus, it would be beneficial to view the ovaries and it may be deemed beneficial to perform an oophorectomy to eliminate the potential for subsequent ovarian pathology. Removing the ovaries reduces the risk of ovarian cancer, which is difficult to detect and often fatal. However, in a large percentage of vaginal hysterectomies, the ovaries are left in the body due to the difficulty in visualizing and excising the ovaries due to the location of the ovaries. In particular, after the removal of the uterus, in a non-insufflated environment, the abdominal cavity collapses into the space formerly occupied by the uterus, concealing the ovaries from view and surgical instruments used by the surgeon. While retractors and graspers can be used to reveal the ovaries to the surgeon, problems still remain in removing them due to their location.

Currently, it is difficult to insufflate the abdominal cavity proximate to the ovaries to increase laparoscopic visibility and instrument maneuvering, as the vagina provides an anatomical opening which would permit any insufflation fluid to escape. While, the Koh device does provide a vaginal seal when used for its particular purpose, it must be held in place, and the opening in the occluder is not adapted to permit the exchange of instruments during a procedure as insufflation gas would escape through the opening during the exchange.

SUMMARY OF THE INVENTION

It is therefore an object of the invention to provide a luminal port assembly particularly adapted for use in the vagina and which aids in the removal of the ovaries after a vaginal hysterectomy.

It is another object of the invention to provide a luminal port assembly for use in the vagina which has means for retaining the port assembly within the vagina.

It is a further object of the invention to provide a luminal port assembly with an external seal which provides a substantially fluid tight seal between the luminal port assembly and the vaginal anatomy.

More broadly, it is an additional object of the invention to provide a valved luminal port assembly insertable into an anatomical passageway.

It is also an object of the invention to provide a luminal port assembly in which the port is angularly movable relative to the external sealing means.

It is still another object of the invention to provide a luminal port assembly having a plurality of valved ports which may be independently angularly movable relative to an external sealing means.

It is yet another object of the invention to provide a luminal port assembly having an insufflation port by which to provide insufflation fluid into an anatomical cavity.

In accord with these objects, which will be discussed in detail below, a luminal port assembly insertable into an anatomical passageway includes a housing having a sealing means for creating a substantially fluid tight seal between the housing and the tissue of the anatomical passageway. At least one port is provided in the housing. The port is provided with a substantially fluid-tight automatic valve, e.g., a tricuspid valve or flapper valve, and is preferably adapted to receive instruments having different diameters (e.g., between 3 mm and 12 mm) therethrough. Preferably, the port is angularly movable relative to the housing, e.g., via the inherent flexibility of the valve components or via an articulable joint such as a ball joint. A retention means is provided for releasably, yet securably, retaining the housing within the anatomical passageway. In addition, a handle assembly, preferably having an insufflation conduit therethrough, may be provided for facilitating the docking and undocking of the housing with the retention means and for insufflating an anatomical cavity distal of the sealing means.

According to a first preferred embodiment of the invention, the sealing means of the luminal port assembly includes an expandable member such as a inflatable membrane which forms a generally toroidal 'balloon' or cuff. Means are provided to control the expansion and contraction, i.e., the inflation and deflation, of the inflatable member. Preferably the expansion and contraction means is a pressurization means, e.g., a fluid supply by which a pressurized fluid may be supplied to or removed from the inflatable membrane. In addition, particularly for vaginal hysterectomy applications, the retention means is a suture ring which is adapted to be positioned adjacent the abdominal cavity and secured thereto with the sutures which were previously used to tie off the vaginal cuff angles. The distal end of the housing may be securely, yet removably, docked to the suture ring to hold the housing in position during a surgical procedure. The luminal port assembly is thereby securely positionable at the desired location for excision of the ovaries.

In accord with one manner of using the first embodiment of the invention, after the uterus has been removed through the vagina, the suture ring is inserted into the vagina to the opening presented into the abdominal cavity. The suture ring is secured in position with suture already located adjacent the vaginal cuff. The luminal port assembly is then inserted into the vagina, preferably maneuverable with the handle assembly, and the distal end of the housing is docked with the suture ring. The inflatable member is then expanded with the pressurization means to create a substantially fluid-tight seal between the interior walls of the vagina and the housing. Once an exterior seal is thereby formed, insufflation gas may be provided into the abdominal cavity through a port in the abdominal cavity. The insufflation gas is prevented from escaping out of the port by the automatic valve and from around the assembly by the inflatable member. Various surgical instruments which range in diameter, e.g., laparoscopic instruments, staplers, and a laparoscope, may then be extended through the automatic valve (which seals around the instruments) in order to remove the ovaries within a facilitative environment. The port may be angularly moved relative to the housing to provide the directional freedom required to access the ovaries. At the conclusion of the operation, the insufflation gas is released, the sealing means is deactivated, and the luminal port assembly is undocked from the suture ring and withdrawn from the vagina. Finally, the suture ring is untied and also removed. As such, the luminal port assembly facilitates the excision of the ovaries after a vaginal hysterectomy.

Several other embodiments of a luminal port assembly utilizing an expandable sealing means are also provided. For example, according to a second embodiment of the invention, the handle assembly includes an insufflation port, obviating the need for a secondary insufflation port through the abdominal cavity. According to a third embodiment of the invention a double lumen conduit is provided for conveying a pressuring fluid to the sealing means through one lumen and for permitting insufflation fluid to be conveyed through the other lumen. According to a fourth embodiment of the invention, the port is provided with a flapper valve and includes an insufflation conduit through which insufflation fluid can be provided. In addition, the port is provided in a member which is coupled to the housing via an articulable joint. According to a fifth embodiment of the invention, two toroidal 'balloons' provide a double external seal. According to a sixth embodiment of the invention, the external seal includes a preferably oval housing having a preferably oval inflation means thereabout. Two ports are provided in the housing, each preferably independently angularly movable relative to the housing. According to a seventh embodiment, which may be used in combination with any of the preceding embodiments, the valve of the valved passageway is located in the port substantially between the proximal and distal ends of the housing.

According to an eighth embodiment, the sealing means comprises at least one opening along the periphery of the housing through which suction is applied to draw the interior vaginal wall about the housing and thereby form the seal. It will be appreciated that in an embodiment in which suction is used as the sealing means, the same suction may also be used as the retention means, securing the luminal port assembly to the walls of the anatomical passageway.

Besides using the luminal port assembly in the vagina, the luminal port assembly may be sized to be received within a different anatomic passageway and form a valved port therein. For example, the luminal port assembly may be positioned within the rectum, esophagus, etc., for the facilitation of surgery therethrough.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
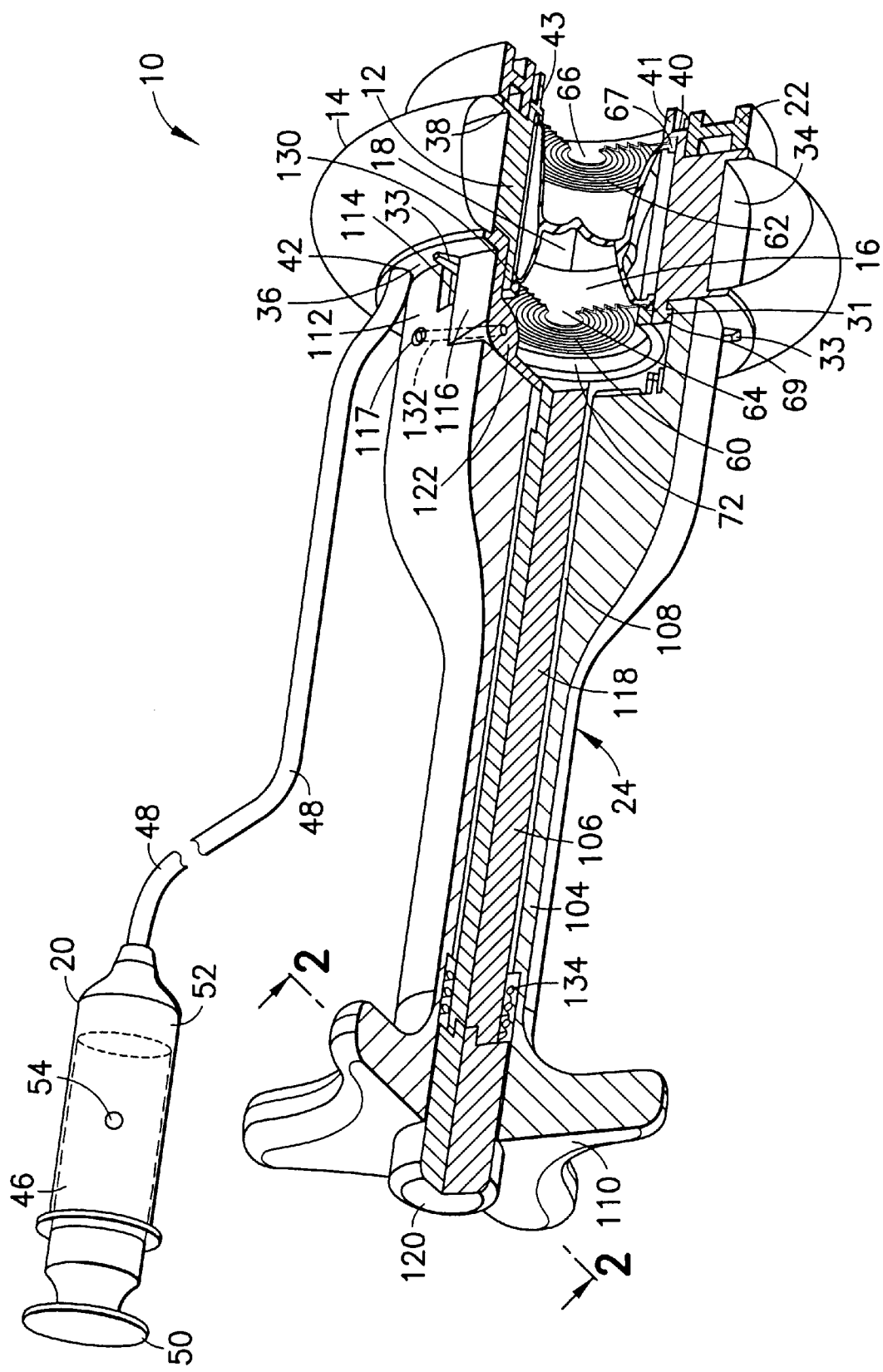
FIG. 1 is a partial section perspective view of a first embodiment of a luminal port assembly according to the invention.
Figure 2:
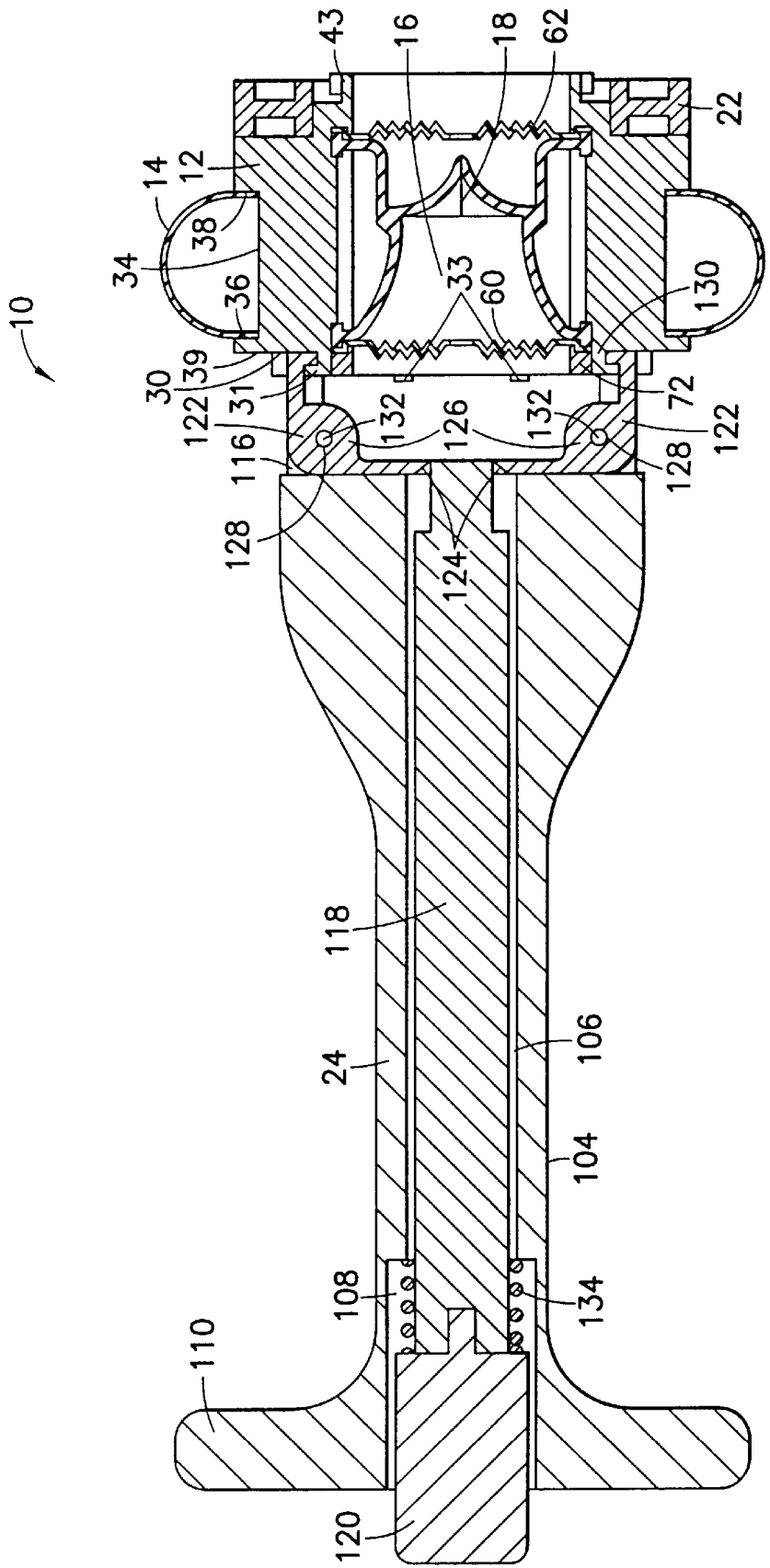
FIG. 2 is a section view across line 2—2 in FIG. 1.

Referring now to FIGS. 1 and 2, a luminal port assembly 10 is provided which is insertable into an anatomical passageway. The luminal port assembly 10 generally includes a housing 12 having an external seal 14 which is adapted to create a fluid-tight seal between the housing and tissue of the anatomical passageway, and a port 16 within the housing provided with a substantially fluid tight valve 18. A pressure-differential means 20 may be used to activate the external seal 14 such that when the luminal port assembly 10 is inserted into an anatomical passageway, the seal 14 may be contacted with the walls of the passageway. A suture ring 22 (retention means) is preferably provided for stabilizing the luminal port assembly 10 within the anatomical passageway, as described below. Preferably, a handle assembly 24 for maneuvering the luminal port assembly into docking relationship with the suture ring 22 is coupled to the housing 12, and may be actuated to be released therefrom.

More particularly, according to a first embodiment of the invention, the housing 12 is generally toroidal in shape and defines a central opening 30. The housing 12 includes a circumferential channel 34 between relatively proximal and distal walls 36, 38. The proximal wall 36 is provided with a hole 42 which extends through the proximal wall and into the channel 34 of the housing 12. The proximal face 39 of the housing 12 includes a circular lip 31 and a plurality of ridges 33 radially spaced about the face 39. The distal portion 43 of the housing 12 includes an interior lip 40 and a short tubular portion 41 which is structurally adapted to securely, yet releasably, dock with the suture ring 22, as described in detail below.

The external seal 14 is preferably an inflatable membrane coupled between the proximal and distal walls 36, 38, thereby forming an inflatable toroidal 'balloon' or cuff about the periphery of the housing 12. The inflatable membrane 14 may be substantially elastic, e.g., rubber, or substantially inelastic but flexible, e.g., vinyl.

The pressure-differential means 20 (i.e., for forming a pressure difference between the interior of the seal 14 and the anatomical passageway) controls the expansion and contraction of the seal 14. The preferable pressure-differential means 20 according to the first embodiment is a pressurization means. Thus, upon activation, it supplies fluid under pressure to the inflatable member, and upon deactivation, it removes fluid from the inflatable member. More particularly, the pressure-differential means 20 is preferably a syringe 46 provided with a gas or liquid (e.g., air or a saline solution) and having a fluid conduit 48 coupled to the hole 42 in the housing 12. As the plunger 50 of the syringe 46 is depressed into the syringe body 52, the fluid within is forced through the fluid conduit 48, through the hole 42 and into the space between the channel 34 of the housing and the membrane 14 to thereby expand the membrane. The plunger 50 may also be at least partially withdrawn from the syringe body 52 to withdraw the fluid and contract the membrane 14. According to a preferred aspect of the invention, the syringe 46 may be adapted to deliver a predetermined volume of fluid by providing a hole 54 in the body of the syringe at the level of the predetermined volume. When the bottom of the plunger 50 is above the hole, no pressure builds within the fluid conduit, as the fluid escapes through the hole 54. Only after the bottom of the plunger 50 passes the hole 42 in the syringe does the pressure build within the seal 14.

The port 16 includes the valve 18, a proximal elastomeric seal 60, and preferably a distal elastomeric seal 62. The proximal and distal seals 60, 62 are each provided with a central opening 64, 66 (about 2.5 mm in diameter), and preferably include corrugations 68, 70 to aid in the flexibility of the seals. The periphery of the distal seal 62 seats against the interior lip 40 of the housing 12. The valve 18 is preferably a duckbill or a tricuspid valve and is also preferably molded to include proximal and distal rims 64, 66. The distal rim 67 seats against the distal seal 62, securing the distal seal 62 against the interior lip 40. The proximal seal 60 seats over the proximal rim 69 and is secured in position by a washer member 72. The port 16 is adapted to receive and seal against a laparoscopic instrument having any size between about 3 mm and 12 mm in diameter through the proximal seal 60, the valve 18 and the distal seal 62; i.e., the port can accommodate instruments across approximately a 9 mm range in size.

Figure 3:
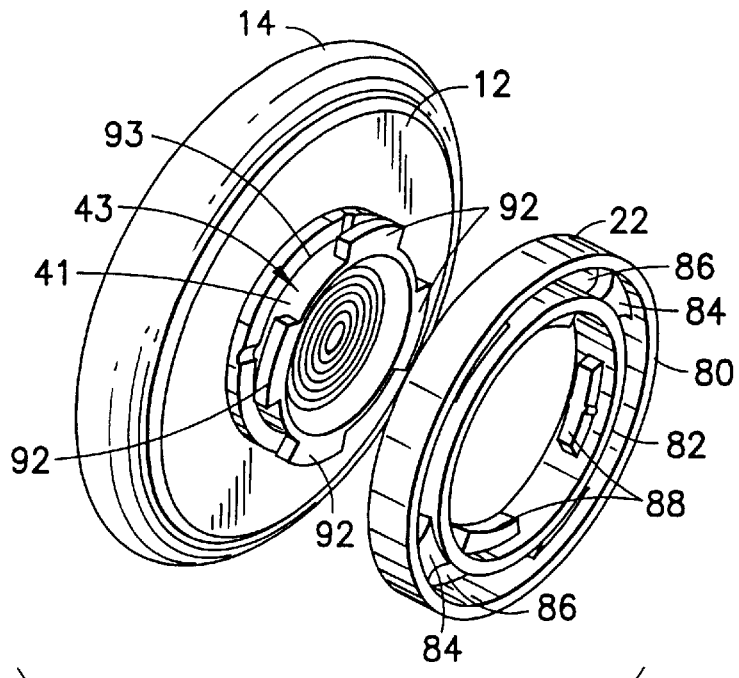
FIG. 3 is a perspective view of the housing and suture ring of the luminal port assembly of FIGS. 1 and 2.
Figure 4:
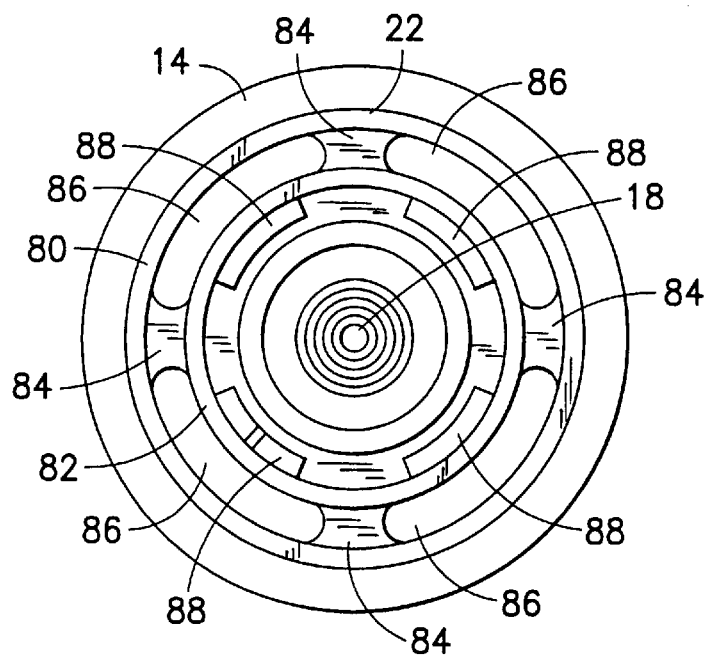
FIG. 4 is a distal end view of the first embodiment of the luminal port assembly according to the invention.

Turning now to FIGS. 3 and 4, the suture ring 22 comprises an external ring portion 80, an internal ring portion 82, a plurality of bridge portions 84 coupling the external and internal ring portions 80, 82 and defining a plurality of openings 86 therebetween, and a plurality of inwardly directed tab portions 88 along the inner circumference of the internal ring portion 82. The distal portion 43 of the housing 12 includes a relatively short tubular extension 41 provided with outwardly directed tab portions 82. The tubular extension 41 may be inserted into the internal ring portion 82 with the outwardly directed tab portions 92 passing between the inwardly directed tab portions 88. The housing 12 may then be rotated relative to the suture ring 22 to the lock the inwardly directed tab portions 88 between a distal face 93 and the outwardly directed tab portions 92 and thereby securely, yet releasably, dock the housing 12 to the suture ring.

Returning to FIGS. 1 and 2, the luminal port assembly 10 is preferably provided with a handle assembly 24 to facilitate the insertion and removal of the luminal port assembly into and from the vaginal passageway and also to facilitate the docking and undocking of the housing with the suture ring 22. The handle assembly 24 includes a stationary member 104 having a longitudinal stepped throughbore 108, and a movable member 106 extending through the throughbore 108 and movable relative thereto. The stationary member 104 includes a proximal handle portion 110 and a distal end 112. The distal end 112 is provided with a plurality of notches 114 for engaging the ribs 33 on the proximal face 36 of the housing 12, and also provided with a pair of diametric slots 116 which intersect the throughbore 108. With respect to each slot 116, a bore 117 extends through the stationary member 104 transversely into the slot. The movable member 106 includes a central shaft 118 provided within the axial throughbore 108, a proximal button 120 having an enlarged diameter relative to the shaft 118 and provided in an enlarged portion of the stepped throughbore 108, and distal locking portions 122. The locking portions 122 are each coupled to the movable member 106 by a live hinge 124. In addition, the locking portions 122 include an enlarged portion 126 having a hole 128 therethrough which defines an axis of rotation for the locking portion 122, and also include a distalmost inwardly-directed engagement flange 130 which locks against the circular lip 31 on the face 36 of the housing 12. Pins 132 are provided in the bores 117 to permit the locking portions 122 to rotate about their axes of rotation. In addition, a spring 134 is provided between the button 120 and the step in the throughbore 108 to bias the button proximally. When the handle assembly 24 is locked to the housing 12, the interlock of the notches 114 about the ribs 33 cause rotation of the handle 110 to rotate the housing 12. It will also be appreciated that by pushing the button 120 such that the movable member 106 moves distally relative to the stationary member 104, the locking portions 122 are caused to rotate about their axes of rotation. As a result, the flange portions 130 on the locking portions 122 release from the circular lip 31 of the housing 12, and thereby release the handle assembly 24 from the housing 12.

In accord with one manner of using the first embodiment of the invention, after a vaginal hysterectomy has been performed, the suture ring 22 is inserted into the vagina to the location of the surgical incision present between the vagina and the abdominal cavity. The suture ring 22 is secured at the opening preferably by tying thereto already present suture material which was used to tie off the vaginal cuff angles during the vaginal hysterectomy procedure. This is facilitated by passing the suture material through the openings 86 in the suture ring 22 and tying the suture to the outer ring portion 80. Once the suture ring 22 is secured, the luminal port assembly 10 is inserted into the vagina by manipulation of the handle assembly 24. The handle assembly 24 is used to maneuver and rotate the housing 12 such that the distal portion 43 of the housing docks with the suture ring 22, as described above. After the luminal port assembly 10 is docked with the suture ring 22, the button 120 is pressed while holding the handle 110 to release the handle assembly 24 from the luminal port assembly 10. The handle assembly is then withdrawn. The external seal 14 may then be inflated with the pressure-differential means 20 to form a sealing 'balloon' or cuff which creates a substantially fluid tight seal between the housing 12 and the interior walls of the vagina. Once an exterior seal is formed, insufflation gas may be provided into the abdominal cavity, e.g., through an abdominal port or via a instrument inserted through the valve 18 and seals 60, 62 of the port 16 itself, to insufflate the abdominal cavity. Surgical instruments, e.g., laparoscopic instruments and a laparoscope, may then be extended through the valve 18 and seals 60, 62 to operate and remove the ovaries within a facilitative environment. The instruments may be angularly moved within the port relative to the housing 12 because of mobility afforded by the flexibility of the corrugated seals 60, 62.

At the conclusion of the operation, the handle assembly 24 is reinserted through the vaginal passageway and proximate to the housing 129 housing 12. The button 110 is then pressed to rotate the locking portions 122 such that the distal flanges 130 are moved into an unlocked position. The distal end of the stationary member 104 is positioned against the face 36 of the housing 12 such that the notches 114 are positioned around the ridges 33. When the button 110 is released, the spring 134 moves the movable member 106 relatively proximally, and the flanges 130 lock against the circular lip 31 on the proximal face 36 of the housing 12 to thereby lock the handle assembly 24 to the housing 12. The handle 110 is rotated to undock the housing from the suture ring 22, and the handle assembly 24 and luminal port assembly 10 are then withdrawn from the vagina. Finally, the suture material securing the suture ring 22 is cut to release the suture ring, which is also removed. As such, the luminal port assembly 10 facilitates the excision of the ovaries after a vaginal hysterectomy.

Figure 5:
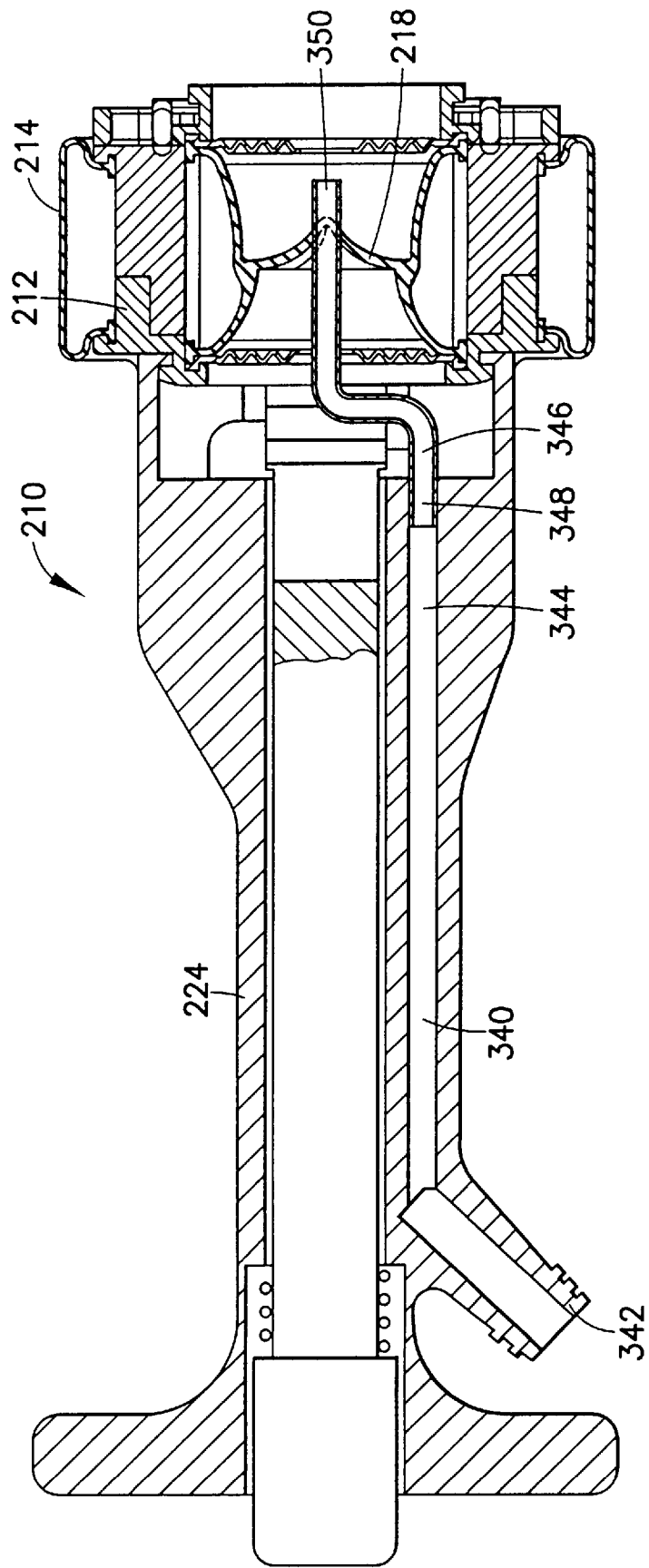
FIG. 5 is a section view of a second embodiment of the luminal port assembly according to the invention which incorporates an insufflation port.

Turning now to FIG. 5, a second embodiment of the luminal port assembly 210 of the invention, substantially similar to the first embodiment (with like parts incremented by 200), is shown. The handle assembly 224 includes an insufflation port 340 having a proximal connector 342, e.g., a luer lock, and an internal passageway 344 in communication with the connector 342. A conduit 346 has a proximal end 348 coupled in the passageway 344 and a distal end 350 extending through the valve 218.

In use, after the housing 212 is docked with the suture ring 222 to secure the luminal port assembly 210 within the vaginal passageway and the sealing means 214 is activated to create a substantially fluid tight seal about the housing 212, insufflation fluid is forced through the insufflation port 340 to insufflate the abdominal cavity. After the abdominal cavity is adequately insufflated, the handle assembly 224 is disengaged from the housing 212 and the conduit 346 is withdrawn from the valve 218, thereby sealing the insufflation gas within the abdominal cavity.

Figure 6:
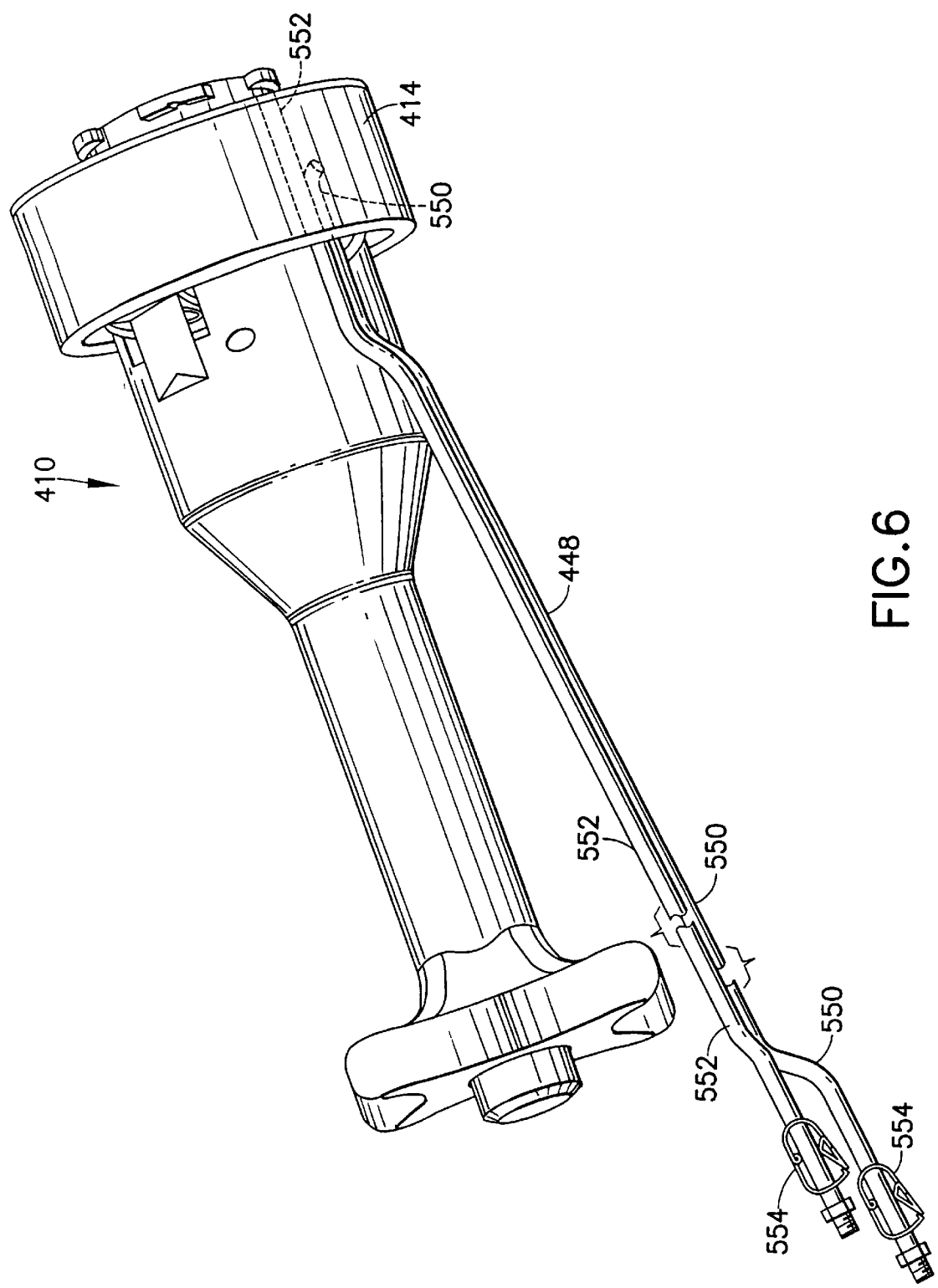
FIG. 6 is a perspective view of a third embodiment of the luminal port assembly according to the invention.

Referring now to FIG. 6, a third embodiment of the luminal port assembly 410 of the invention, substantially similar to the first embodiment (with like parts incremented by 400), is shown. A double lumen conduit 448 is coupled to the housing 412. A first lumen 550 is provided for conveying a pressuring fluid to the sealing means 414, as described above, and the second lumen 552 is provided for the passage of insufflation fluid therethrough. As such, the second lumen 552 extends through to the distal side of the housing 412. Clamps 554 may be provided along the conduit 448 for preventing a backflow of fluid through the lumen.

Figure 7:
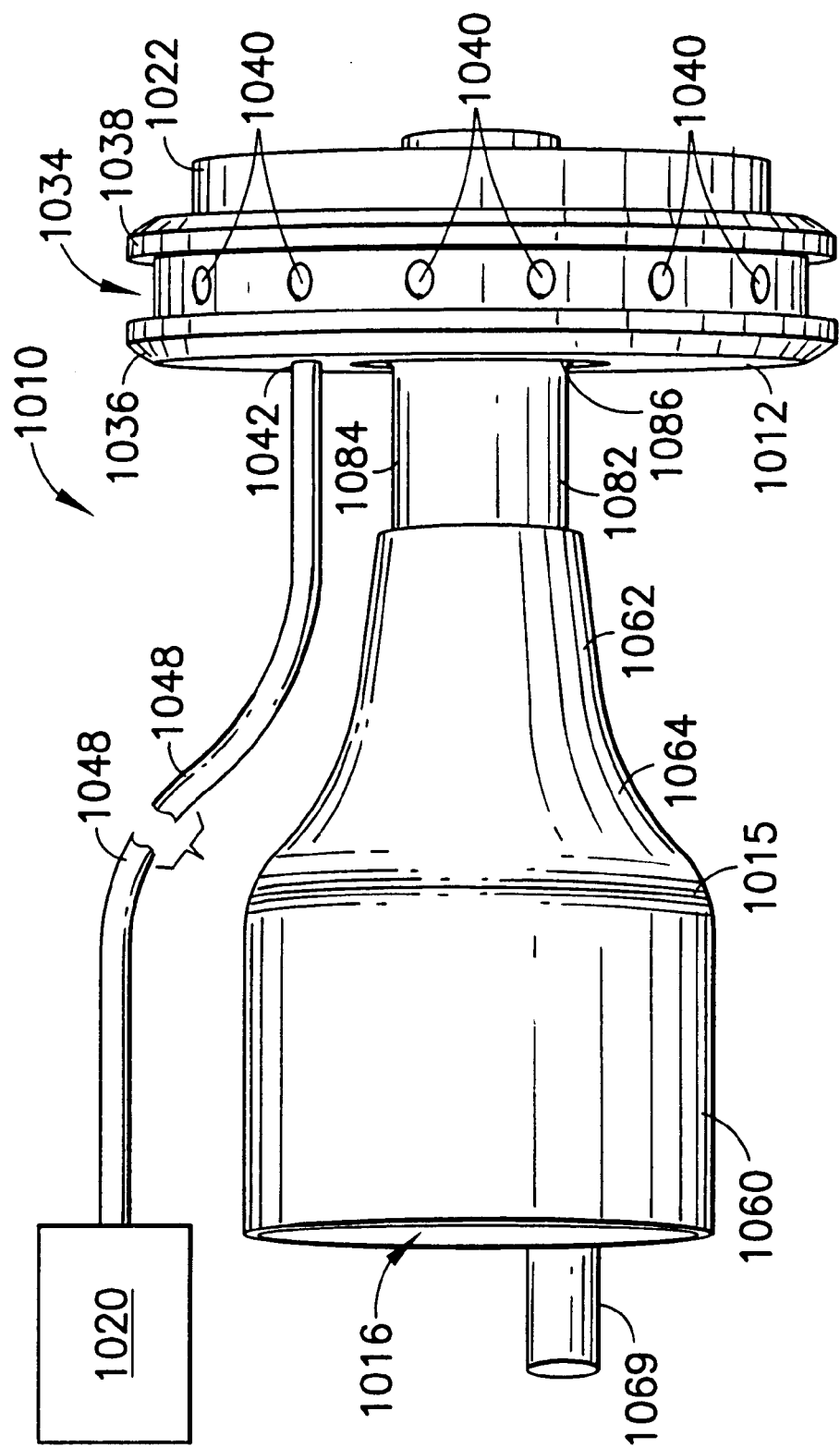
FIG. 7 is a broken perspective view of a fourth embodiment of a luminal port assembly with an extended housing according to the invention, and shown without the sealing means.
Figure 8:
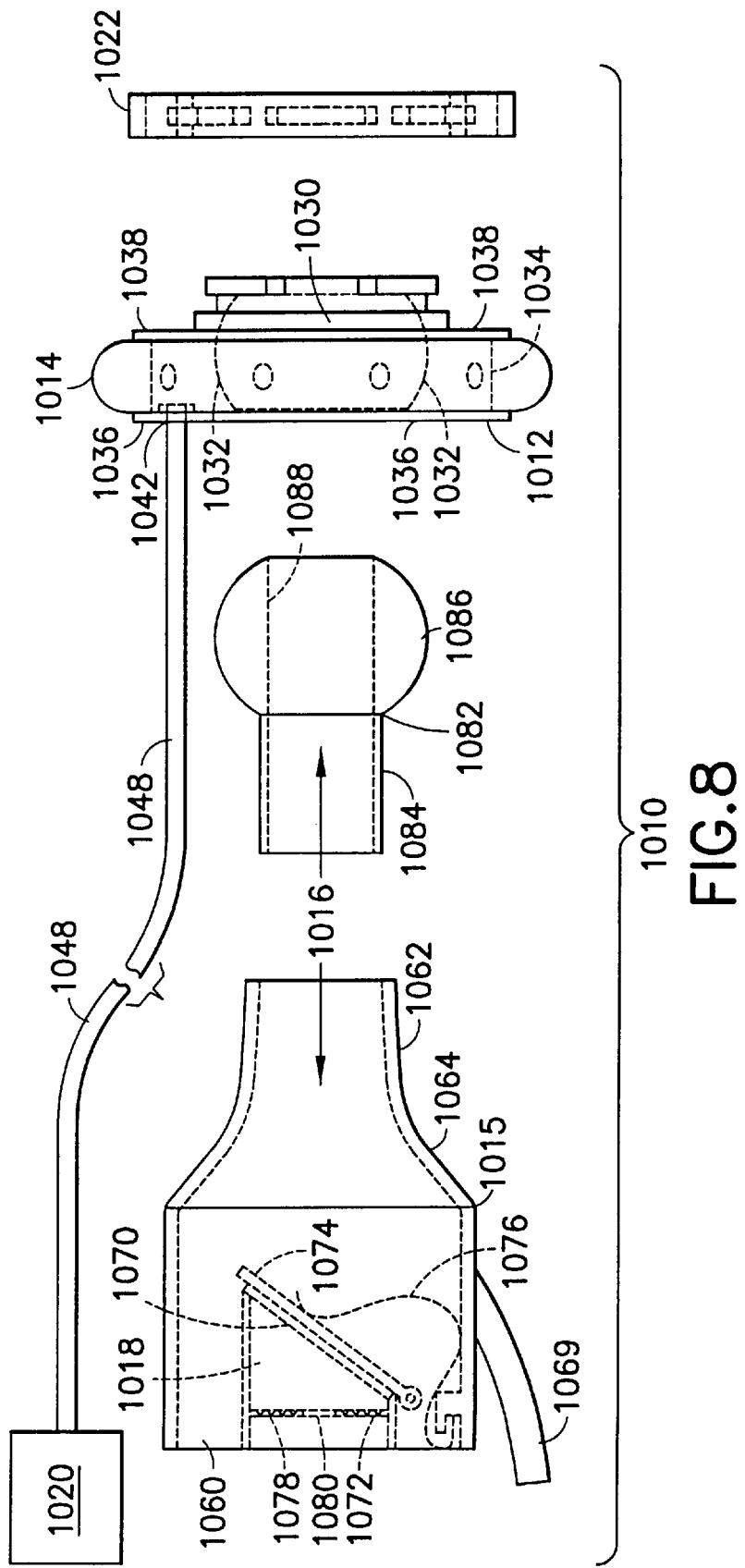
FIG. 8 is an exploded view of the fourth embodiment of the luminal port assembly according to the invention.

Turning now to FIGS. 7 and 8, a fourth embodiment of a luminal port assembly 1010 substantially similar to the first embodiment is shown. The housing 1012 is generally toroidal in shape and defines a central opening 1030. The central opening 1030 preferably includes spherically arced interior walls 1032 (FIG. 8). The housing 1012 also includes a circumferential channel 1034 between relatively proximal and distal walls 1036, 1038. The proximal wall 1036 is provided with a hole 1042 into the interior of the housing 1012. In addition, the channel 1034 is provided with a plurality of circumferential holes 1040 into the interior of the housing 1012. Upon activation of the pressure differentiation means 1020, fluid is forced through the fluid conduit 1048, into the interior of the housing 1012, through the circumferential holes 1040, and into the channel 1034 which is covered by the sealing means 1014 in order to expand the sealing means.

The housing 1012 includes a port member 1015 having a preferably cylindrical proximal portion 1060, a distal neck portion 1062 preferably of relatively smaller diameter, and a central portion 1064 which preferably tapers between the proximal and distal portions, and defining a port 1016. The proximal portion 1060 (or any other portion of the port member 1015) includes the substantially fluid tight valve 1018 and preferably an insufflation conduit 1069 having a proximal end couplable to an insufflation gas supply and a distal end which opens distal of the valve 1018. The valve 1018 is preferably a flapper valve and includes a preferably angled distal portion 1070 preferably provided with a resilient seal 1072 thereover, an openable and preferably rotatable flapper lid 1074, and a spring 1076 which biases the lid 1074 against the seal 1072 to compress the seal 1072 and provide the valve 1018 with substantially fluid-tight properties. An elastomeric septum 1078 having a central opening 1080 is preferably provided in the proximal portion of the valve 1018. The port 1016 is adapted to receive a laparoscopic instrument through the septum 1078 and beyond the distal portion 1070, forcing the flapper lid 1074 into an open position, as described in detail below.

The port member 1016 is preferably coupled to the housing 1012 via a member 1082 having a proximal stem 1084 and a ball joint 1086 which together define a cylindrical opening 1088 therethrough. The stem 1084 of the member 1082 is preferably solvent bonded to the neck portion 1062 of the port assembly 1016. The ball joint 1086 is received within the arced interior walls 1032 of the housing 1012, thereby forming a ball and socket joint. As a result, the port member 1015, and therefore the port 1015, is articulable in at least two dimensions relative to the housing 1012. The articular ball and socket may be used with any embodiment of the luminal port assembly described herein.

Figure 9:
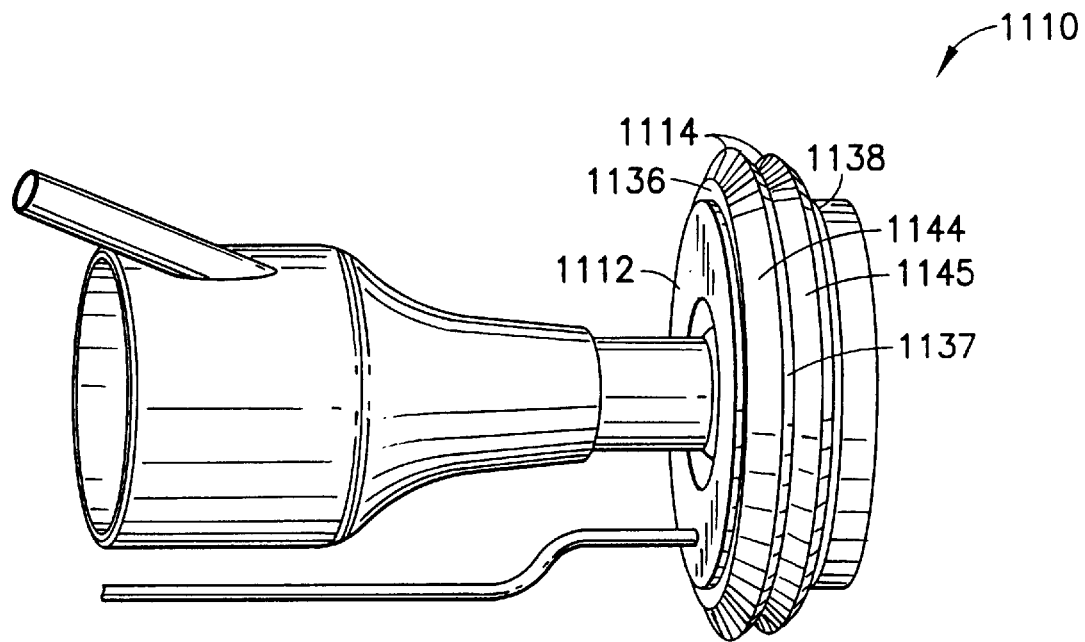
FIG. 9 is a perspective view of a fifth embodiment of the luminal port assembly with a double external seal according to the invention.

Turning now to FIG. 9, a fifth embodiment of the luminal port assembly 1110, substantially similar to the fourth embodiment (with like parts having numbers incremented by 100 relative thereto) is shown. The housing 1112 includes a proximal wall 1136, a central wall 1137, and a distal wall 1138. A first inflatable membrane 1144 is coupled between the proximal and central walls 1136, 1137, and a second inflatable membrane 1145 is coupled between the central and distal walls 1137, 1138, thereby forming two inflatable 'balloons' about the periphery of the housing 1112. This double seal 1114 may enhance the ability to create a fluid-tight seal between the periphery of the housing and the vaginal wall, and may be used with any of the other embodiments described herein.

Figure 10:
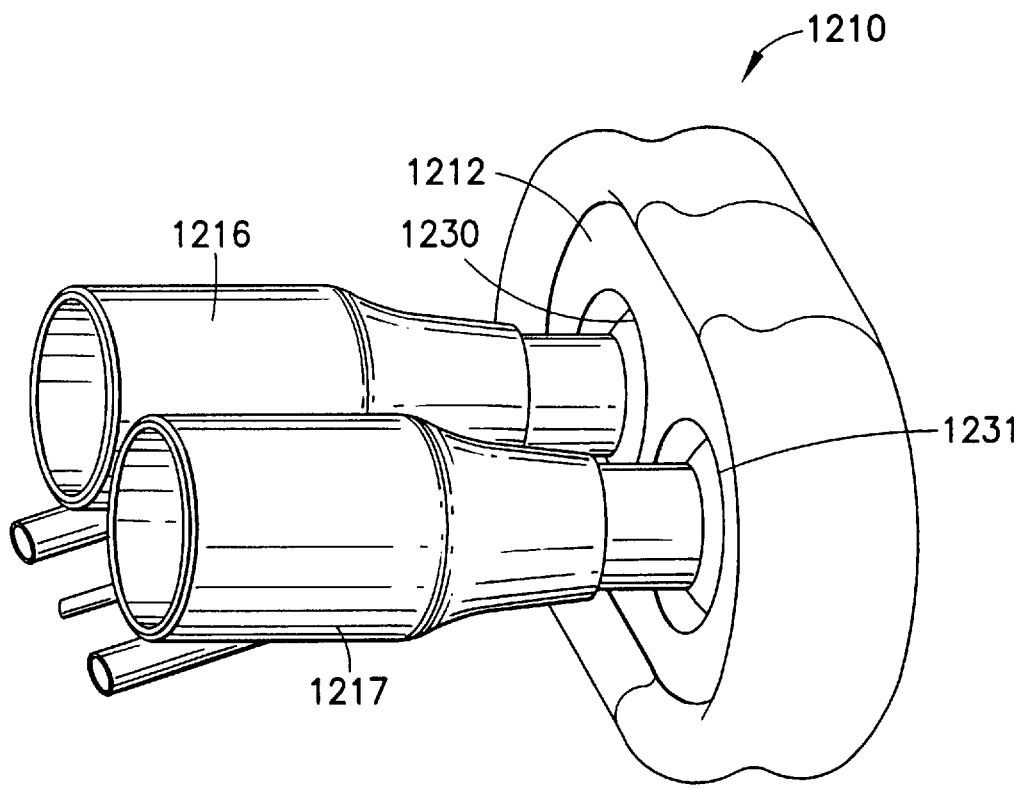
FIG. 10 is a perspective view of a dual ported sixth embodiment of the luminal port assembly according to the invention.

Referring now to FIG. 10, a sixth embodiment of the luminal port of the invention, substantially similar to the fourth embodiment (with like parts having numbers incremented by 200 relative thereto) is shown. The housing 1212 includes two generally central openings 1230, 1231 in its preferably substantially oval configuration. First and second ports 1216, 1217 are coupled in the openings 1230, 1231, preferably such that they are angularly movable relative to the housing 1212.

Figure 11:
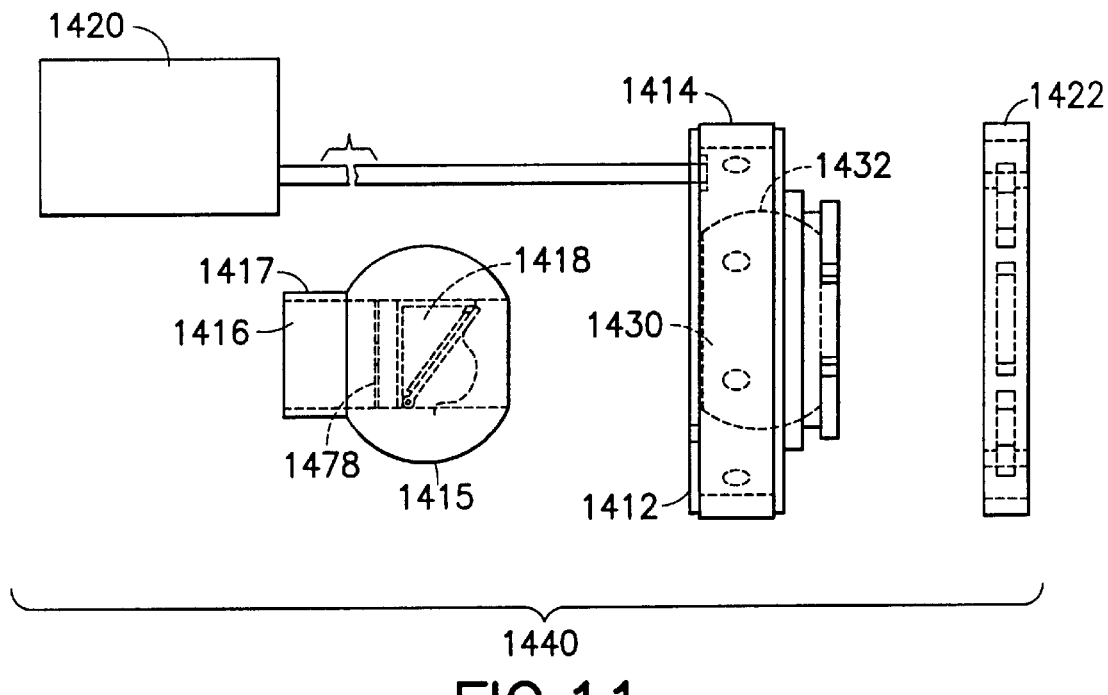
FIG. 11 is an exploded view of a luminal port assembly with an angularly movable port according to a seventh embodiment of the invention.
Figures 12, 13:
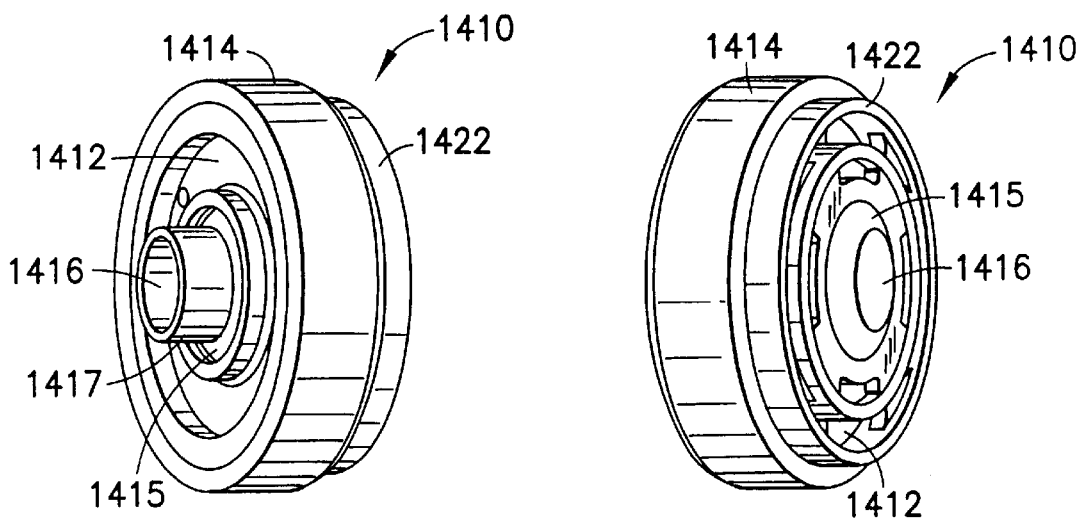
FIG. 12 is a proximal perspective view of the seventh embodiment of the luminal port assembly according to the invention, with means for activating the sealing means not shown.
FIG. 13 is a distal perspective view of the seventh embodiment of the luminal port assembly according to the invention.

Referring now to FIGS. 11 through 13, a seventh embodiment of a luminal port assembly 1410 according to the invention is shown. The luminal port assembly includes a housing 1412 having a port member 1415 defining a port 1416, a sealing means 1414 and means for activating the sealing means 1420, and a retention means 1422. The port member 1415 has a generally spherical form and preferably includes a proximal tubular portion 1417. The housing 1412 has a diameter greater than its length. The port member 1415 is provided within spherical curved walls 1432 of the housing 1412, thereby permitting articulation of the port member (and the port) relative to the housing. A valve 1418 as well as one or more resilient washer-like seals 1478 are provided within the port member 1415. A port thusly designed permits a large range of movement when the luminal port is utilized within relatively long anatomically passageways such as the vaginal canal. It will be appreciated that the port member 1415, as described, may be used in any of the embodiments described herein. Moreover, it will be appreciated that the seventh embodiment is adaptable for use with the above described handle assembly 24.

Figure 14:
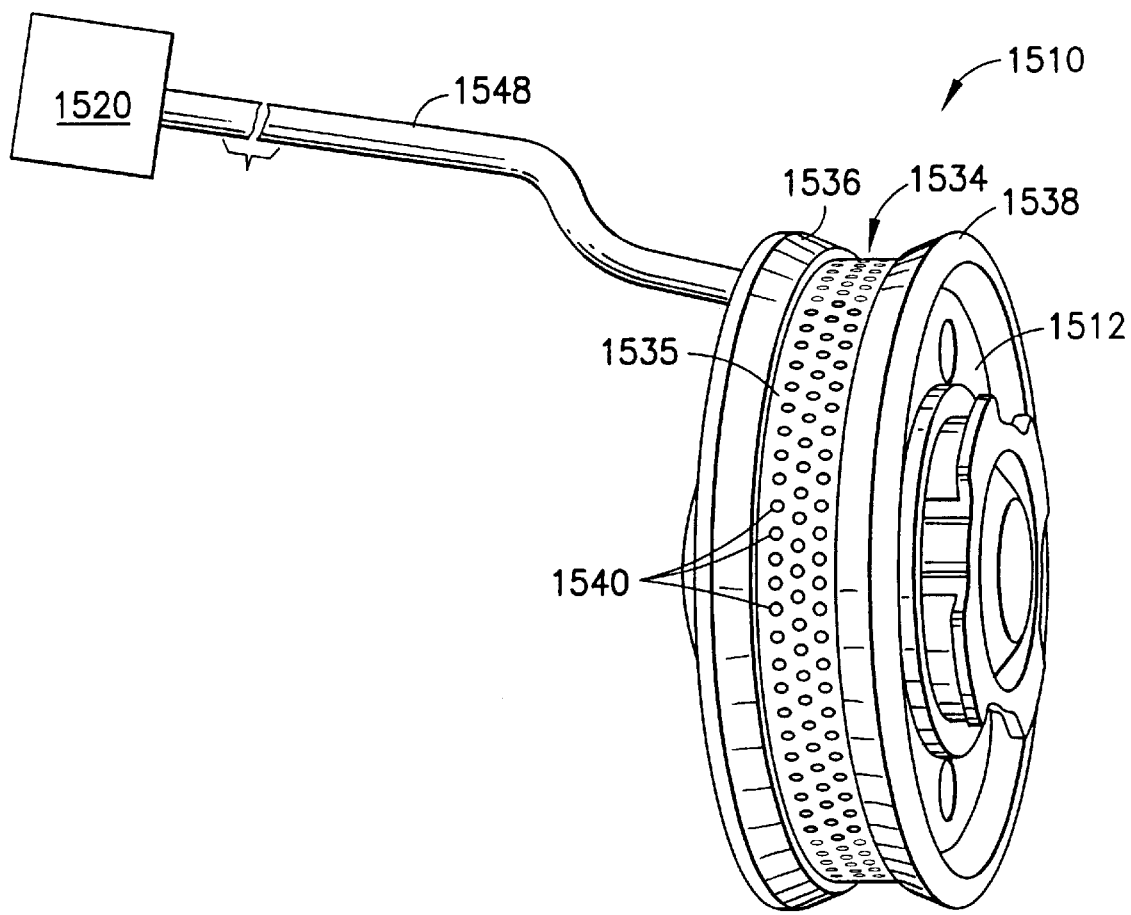
FIG. 14 is a perspective view of an eighth embodiment of the luminal port assembly according to the invention utilizing suction.

Turning now to FIG. 14, an eighth embodiment of the luminal port assembly 1510 according to the invention is shown. The housing 1512 includes a proximal wall 1536 and a relatively distal wall 1538 defining a channel 1534 therebetween. The floor 1535 of the channel 1534 is provided with a plurality of openings 1540 into the interior of the housing. A pressure-differential means 1520 in the form of a suction means is coupled to the housing 1512 via a conduit 1548 coupled to a hole in the housing. When suction is applied by the suction means 1520, fluid is removed from within the channel 1534 via the holes 1540 and a vacuum is formed about the periphery of the housing 1512. The force of the vacuum may be used to draw the interior vaginal wall about the housing 1512 to thereby form a seal. In addition, the vacuum pressure also functions to retain the luminal port within the vaginal passageway, and as such may also performs as the retention means (although docking tabs are provided so that a retention ring may be utilized, if desired). Removing the suction releases the vaginal tissue from the periphery of the housing. Moreover, it will be appreciated that the eighth embodiment is adaptable for use with the above described handle assembly 24.

There have been described and illustrated herein several embodiments of a luminal port assembly. While particular embodiments of the invention have been described, it is not intended that the invention be limited thereto, as it is intended that the invention be as broad in scope as the art will allow and that the specification be read likewise. Thus, while particular configurations of the assembly have been disclosed, it will be appreciated that other configurations may be used as well. While the luminal port assembly has been particularly described for use in the vagina, the luminal port assembly may also be sized to be received within a different anatomically passageway and form a valved port therein. For example, the luminal port assembly may be sized to be positioned within the rectum for the facilitation of surgery on the colon therethrough. Likewise, the luminal port may be sized to form sealed ports in other anatomical passageways, including, but not limited to, the esophagus, nostrils, and ear canals. In addition, in particular applications the suture ring may not be required, and for such applications the distal portion of the housing may be configured without the structure for docking with the suture ring. Furthermore while particular types of sealing means and means for activating the sealing means have been disclosed, it will be understood that other expandable sealing means can be used. For example, and not by way of limitation, the sealing means may be mechanically expandable. Also, while a particular configuration of a suction-type sealing means has been disclosed, it will be recognized that other configurations which provide suction about the periphery of the housing for the port may be utilized. Moreover, other structures which permit a substantially fluid tight seal about the periphery, whether by expansion, suction, or otherwise, of the housing may be used. Also, while the pressure-differential means has included a flexible conduit coupled through the housing to a channel surrounding the sealing means, it will be appreciated that in the embodiments comprising an inflatable member, the conduit of the pressure-differential means may be directly coupled to the inflatable member. Furthermore, while several ways of coupling a port member within the housing have been disclosed, it will be understood that other couplings which preferably permit movement of the port member within the housing can be similarly used. In addition, while two valve constructs have been disclosed, it will be appreciated that many different valve constructs are known in the art and it is intended that any suitable valve may be used with the invention; although it is particularly desirable that the valves seal against tools having diameters which differ by a range of 5 mm or more. Also, while the luminal port assembly is described as comprising a housing having a port provided with a valve, it will be appreciated that the assembly may be constructed to comprise the housing and sealing means and be adapted to couple with an off-the-shelf valved port, e.g., a trocar port. It will therefore be appreciated by those skilled in the art that yet other modifications could be made to the provided invention without deviating from its spirit and scope as so claimed.

What is claimed is:

1. A luminal port assembly for insertion into an anatomical passageway having tissue adjacent thereto, comprising:
   a) a housing with a port having a valve therein;
   b) sealing means for creating a substantially fluid tight seal between at least a portion of said housing and the anatomical passageway; and
   c) retention means adapted to be coupled to the tissue for retaining the luminal port assembly within the anatomical passageway.

2. A luminal port assembly according to claim 1, wherein:
   said port is comprised of a tubular member which includes said valve, and said tubular member is angularly movable relative to said housing.

3. A luminal port assembly according to claim 2, wherein:
   said tubular member is articulable in at least two dimensions relative to said housing.

4. A luminal port assembly according to claim 1, wherein:
   said sealing means defines a substantially toroidal shape.

5. A luminal port assembly according to claim 1, wherein:
   said sealing means includes an inflatable member.

6. A luminal port assembly according to claim 1, wherein:
   said housing is provided with a hollow, a periphery, and at least one opening between said periphery and said hollow, and
   said sealing means includes an inflatable member about said periphery and in fluid communication with said at least one opening such that providing a pressurized fluid into said hollow causes said inflatable member to inflate.

7. A luminal port assembly according to claim 6, wherein:

said sealing means comprising at least two inflatable members about said periphery and in fluid communication with said at least one opening such that providing a pressurized fluid into said hollow causes said at least two inflatable members to inflate.

8. A luminal port assembly according to claim 1, wherein:

said sealing means includes a pressure-differential means for creating a pressure differential, and said sealing means applies said pressure differential between a periphery of said housing and the anatomical passageway.

9. A luminal port assembly according to claim 8, wherein:

said pressure-differential means creates a negative pressure.

10. A luminal port assembly according to claim 9, wherein:

said means for retaining said housing is said negative pressure.

11. A luminal port assembly according to claim 1, wherein:

said housing has a length and a diameter greater than said length.

12. A luminal port assembly according to claim 1, wherein:

said housing has a periphery, and said means for retaining said housing in said anatomical passageway is a means for creating a negative pressure about said periphery of said housing.

13. A luminal port assembly according to claim 1, wherein:

said means for retaining said housing in said anatomical passageway is removably securely couplable to a distal portion of said housing.

14. A luminal port assembly according to claim 1, wherein:

said at least one port is at least two ports.

15. A luminal port assembly according to claim 14, wherein:

each of said at least two ports is independently angularly movable relative to said housing.

16. A luminal port assembly according to claim 1, wherein:

said port is further provided with at least one resilient diaphragm having a instrument-receiving hole therein.

17. A luminal port assembly according to claim 16, wherein:

said port is adapted to substantially fluid-tightly receive instruments having a diameter size range from about 3 mm to about 12 mm.

18. A luminal port assembly according to claim 1, wherein:

said port is adapted to substantially fluid-tightly individually receive various instruments which have a 5 mm variance in size.

19. A luminal port assembly according to claim 1, wherein:

said valve is one of a duckbill valve, flapper valve and a tricuspid valve.

20. A luminal port assembly according to claim 1, further comprising:

e) a handle means for maneuvering said luminal port assembly within anatomical passageway, said handle means couplable to and uncouplable from said housing.

21. A luminal port assembly according to claim 20, wherein:

said handle means includes a longitudinal axis, a first member provided with a throughbore parallel to said longitudinal axis, and a second member at least partially received within said throughbore and biased proximally within said throughbore by a spring means, said second member including distal engaging means for releasably engaging said housing and being disengaged from said housing upon distal movement of said second member relative to said first member.

22. A luminal port assembly according to claim 20, wherein:

said handle means is provided with an insufflation conduit for providing an insufflation fluid through said valve.

23. A seal and retention assembly for receiving a port having a valve, said assembly and the port for insertion into an anatomical passageway having tissue adjacent thereto, said seal and retention assembly comprising:

a) a housing defining an opening in which the port is couplable;

b) sealing means for creating a substantially fluid tight seal between at least a portion of said housing and the anatomical passageway; and c) retention means adapted to be coupled to the tissue for retaining the luminal port assembly within the anatomical passageway.

24. A seal and retention assembly according to claim 23, wherein:

said opening defines walls which are substantially spherically curved.

25. A seal and retention assembly according to claim 23, wherein:

said housing has a substantially toroidal shape.

26. A seal and retention assembly according to claim 23, wherein:

said sealing means includes an inflatable member.

27. A seal and retention assembly according to claim 23, wherein:

said housing is provided with a hollow, a periphery, and at least one opening between said periphery and said hollow, and said sealing means includes an inflatable member about said periphery and in fluid communication with said at least one opening such that providing a pressurized fluid into said hollow causes said inflatable member to inflate.

28. A seal and retention assembly according to claim 27, wherein:

said sealing means comprising at least two inflatable members about said periphery and in fluid communication with said at least one opening such that providing a pressurized fluid into said hollow causes said at least two inflatable members to inflate.

29. A seal and retention assembly according to claim 23, wherein:

said sealing means includes a pressure-differential means for creating a pressure differential between said periphery of said housing and the anatomical passageway.

30. A seal and retention assembly according to claim 23, wherein:

said pressure-differential means creates a negative pressure at a periphery of said housing relative to said anatomical passageway.

31. A seal and retention assembly according to claim 23, wherein:

said housing has a length and a diameter greater than said length.

32. A seal and retention assembly according to claim 23, wherein:

said housing has a periphery, and said means for retaining said housing in said anatomical passageway is a means for creating a negative pressure about said periphery of said housing.

33. A seal and retention assembly according to claim 23, wherein:

said means for retaining said housing in said anatomical passageway is removably securely couplable to a distal portion of said housing.

34. A seal and retention assembly according to claim 23, wherein:

said port is adapted to substantially fluid-tightly receive instruments having a diameter size range from about 3 mm to about 12 mm.

35. A seal and retention assembly according to claim 23, wherein:

said port is adapted to substantially fluid-tightly individually receive various instruments which have up to a 5 mm variance in size.

36. A luminal port assembly for insertion into an anatomical passageway having tissue adjacent thereto, comprising:

a) a housing with a port having a valve therein an entirety of, said valve being angularly movable relative to said housing; and b) sealing means for creating a substantially fluid tight seal between at least a portion of said housing and the anatomical passageway.

37. A luminal port assembly according to claim 36, wherein:

said entirety of said is articulable relative to said housing.

38. A luminal port assembly according to claim 36, wherein:

said housing includes a plurality of ports, each having a valve therein entireties, said valves being independently angularly movable relative to said housing.

39. A luminal port assembly according to claim 36, further comprising:

c) retention means adapted to be coupled to the tissue for retaining the luminal port assembly within the anatomical passageway.

40. A luminal port assembly for insertion into an anatomical passageway having tissue adjacent thereto, comprising:

a) housing with a port having a valve therein, said port adapted to substantially fluid-tightly individually receive various instruments which have a 5 mm variance in size; and b) sealing means for creating a substantially fluid tight seal between at least a portion of said housing and the anatomical passageway.

41. A luminal port assembly according to claim 40, wherein:

said port is adapted to substantially fluid-tightly receive instruments having a diameter size range from about 3 mm to about 12 mm.

* * * * *